(12) United States Patent  
Fiz

(10) Patent No.: US 6,241,731 B1  
(45) Date of Patent: Jun. 5, 2001

(54) PLATE AND SCREW ASSEMBLY FOR FIXING BONES

(76) Inventor: Daniel Fiz, Alvarez Thomas 198 - 4° Floor "H", (C1427CCO) Capital Federal (AR)

( * ) Notice: Subject to any disclaimer, the term of this patent is extended or adjusted under 35 U.S.C. 154(b) by 0 days.

(21) Appl. No.: 09/293,438

(22) Filed: Apr. 16, 1999

(30) Foreign Application Priority Data

Aug. 11, 1998 (AR) .............................................. 980103959

(51) Int. Cl.[7] .................................................... A61B 17/56

(52) U.S. Cl. ................................. 606/65; 606/69; 606/72

(58) Field of Search ................................. 606/65, 62, 61, 606/72, 73, 68, 69, 70, 71; 411/427, 317, 314

(56) References Cited

U.S. PATENT DOCUMENTS

| 5,053,036 | * | 10/1991 | Perren et al. | 606/69 |
| 5,676,666 | * | 10/1997 | Oxland et al. | 606/61 |
| 5,797,912 | * | 8/1998 | Runciman et al. | 606/69 |
| 5,976,141 | * | 11/1999 | Haag et al. | 606/72 |

* cited by examiner

Primary Examiner—Henry J. Recla  
Assistant Examiner—Lien Ngo  
(74) Attorney, Agent, or Firm—Darby & Darby

(57) ABSTRACT

Plate and screw assembly for fixing bone pieces, the assembly including a plate and at least one screw, the plate including at least one orifice that defines a cavity for housing a head of the screw and the screw head is provided with a resilient retainer for retaining the head of the screw within the cavity with free pivotal movement but prevented from any axial movement, so that the screw is prevented from moving out of the orifice of the plate.

6 Claims, 2 Drawing Sheets

PLATE AND SCREW ASSEMBLY FOR FIXING BONES

BACKGROUND OF THE INVENTION

1. Field of the Invention

The present invention relates to the field of bone fixation wherein two or more bone parts, for example pieces of a broken bone, must be kept together to be firmly welded, for example, and more particularly the invention relates to an assembly formed by at least one plate and a screw, the assembly being of the type wherein the plate is provided with at least one orifice transversally passing through the plate with the orifice receiving the screw and the screw being provided with an upper head that is housed into a cavity defined into the orifice.

2. Description of the Prior Art

It is well known that in treatments of degenerative spine disc pathologies, traumas and tumors, for example, plates for promoting the bone welding are used, wherein the plates are placed and fixed to the bone pieces in order to firmly and rigidly keep the pieces in position relative to each other, the plates being fixed to the bone pieces by screws that are passed through orifices in the plates and screwed into the bone pieces.

Once the plate has been placed and fixed to the bones and the wounds resulting from the surgical operation have been closed, the patient lives the hospital and the normal movements of the patient may cause small relative movements of the bone pieces under fixation which causes the screws to be moved and get loose enough to be released from the corresponding orifice of the plate. Under these circumstances the patient undergoes a potential risk that the head of the screw moves out of the orifice and enters into contact with tissues and sensitive parts of the patient's body.

Among the several solutions provided to overcome this problem it may be found a technique of deforming or distorting the head of the screw with the purpose of creating points or areas providing a high friction contact between the screw head and the orifice in the plate. This distortion is performing once the screw has been screwed into the patient's bone and is obtained by hammering the screw head with the help of a tool set, such as a hammer and a punch or a stamp. Intensive care must be taken, however, to avoid any risk for the patient that would affect any closer sensitive organ, spinal cord, marrow, etc. In addition, the firm and safe fixation of the screw within the orifice is not guaranteed as long as the distortions are not seriously programmed but they are aleatory.

In other situations the plate is provided with an extra small orifice adjacent to the orifice for the fixation screw, the small orifice receiving an additional small extra screw. Once the fixation screw has been screwed into the bone the extra small screw is inserted and screwed into the orifice of the plate with the purpose that a head of the extra screw enters into forced contact with the head of fixation screw in order to create a mutual interference to avoid the loosening of the fixation screw. It is obvious that this attempt not only does not guarantee a solution as long as the extra screw is also subject to the risk of getting loose from the associated orifice but also this screw creates an additional risk to the patient because this extra screw will be subject to any movement of the fixation screw, that is, the extra screw would be released from the plate in a period of time shorter than the period of time the fixation screw would get loose.

Another attempt to firmly retain the fixation screw in place it has been to provide a small disc covering at least part of the fixation screw once it is placed and screwed in position, the disc being installed and fixed on the plate by a central small screw passing through the disc and screwed into the plate. Again, a new screw, that is a new problem, is provided with the risk being increased for the patient. In this situation, if the small screw of the disc gets loose, not only the small screw will affect the patient but also the disc that gets free within the patient's body.

Another device developed by the patentee of this application is revealed in U.S. patent application Ser. No. 09/154997 for a "BONE FIXATION DEVICE" consisting of a disc-like piece that is riveted to the fixation plate thus avoiding the use of screws and loose parts, the disc-like piece having radial projections and being capable of rotate against a strong friction resistance created between the piece and the fixation plate to avoid any undesired rotation and movement of the disc piece. The disc-like piece is rotatably riveted to the plate, close to the orifice or orifices receiving the fixation screw or screws, and the disk-like piece can be manually rotated so as to place the radial projections over the heads of the fixation screws once they are placed and screwed in the corresponding orifices of the plate. Thus, the heads of the fixation screws remain covered by the corresponding radial projection and prevented from moving out of the corresponding orifice even when getting loose under the effects of the movements of the patient.

As it is apparent from the above description all the solutions appeal to the provision of additional outer elements like screws and discs or plates fixed to the fixation plate with the purpose of forming an interference or blocking to the head of the fixation screw after the fixation screw has been screwed into the bone pieces, with all these additional elements representing not only an additional task for the surgeon but also a risk for the patient by projecting out of the plate and causing a trauma to the patient.

It well known to any person skilled in the art that in a surgery room any additional element or tool results in the need of additional personnel and time for manipulating the elements and to carry out the complex and time consuming task derived from the additional procedures.

It would be therefore convenient to have a new bone fixation assembly that does not need of additional elements that must be handled out of the conventional and necessary fixation plate and screws, wherein the assembly is formed by the essential two basic elements and guarantee a firm an safe permanent retention of the screw into the bone and the plate.

3. Summary of the Invention

It is therefore one object of the present invention to provide a bone fixation assembly comprised of the two essential basic components, namely the fixation plate and the fixation screw, without additional outer elements being provided to be manipulated by the surgery room personnel but the firm and safe retention being guaranteed by retention means safely forming part of the screw.

It is a further object of the invention to provide a plate and screw assembly for fixing bones wherein the plate is provided with at least one orifice having a cavity an the screw is provided with self retaining means that forms part of the screw and provides the necessary resistant force to retain the head against any axial movement once the head of the screw is housed inside the cavity, whereby the head can pivotally move but is prevented from moving out of the cavity, even if the screw has been released from the bone.

It is another object of the present invention to provide plate and screw assembly for fixing bone pieces, the assembly including a plate and at least one screw, the plate including at least one orifice that defines a cavity for housing a head of the screw and the screw head is provided with a resilient retainer for retaining the head of the screw within the cavity with free pivotal movement but prevented from any axial movement, so that the screw is prevented from moving out of the orifice of the plate.

It is still another object of the present invention to provide a plate and screw assembly for use in bone fixation, applied in procedures of joining bone pieces for the welding of the pieces, the assembly being of the type including a plate and at least one screw, the plate including at least one orifice passing through the plate, the orifice defining a housing cavity for housing a head of the screw passing through the orifice, the screw being passed through the orifice and screwed into one of the bone pieces to firmly retain the plate against the bone pieces to be joined together, wherein the head of the screw has resilient means capable of being retained, together with the screw head, inside the housing cavity against any axial movement, whereby the head of the screw being prevented from axially moving back out of the cavity.

It is a further object of the present invention to provide a plate and screw assembly for use in bone fixation, applied in procedures of joining bone pieces for the welding of the pieces, the assembly being of the type including a plate and at least one screw, the plate including at least one orifice passing through the plate, the orifice defining a housing cavity for housing a head of the screw passing through the orifice, the screw being passed through the orifice and screwed into one of the bone pieces to firmly retain the plate against the bone pieces to be joined together, wherein the housing cavity has an upper opening and a lower opening, an intermediate portion being defined inside the cavity between the openings, the intermediate portion having a diameter larger than any diameter of the upper and lower openings, the screw defining a longitudinal axis and the screw head including a resilient cap retained in the head against any axial movement and capable of radially normally yielding relative to the screw axis to enter into the cavity and radially normally expanding back relative to the screw axis to be retained into the cavity together with the head of the screw once inside the cavity, whereby the head of the screw, and hence the screw, being prevented from axially moving back out of the cavity.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Figure 1:
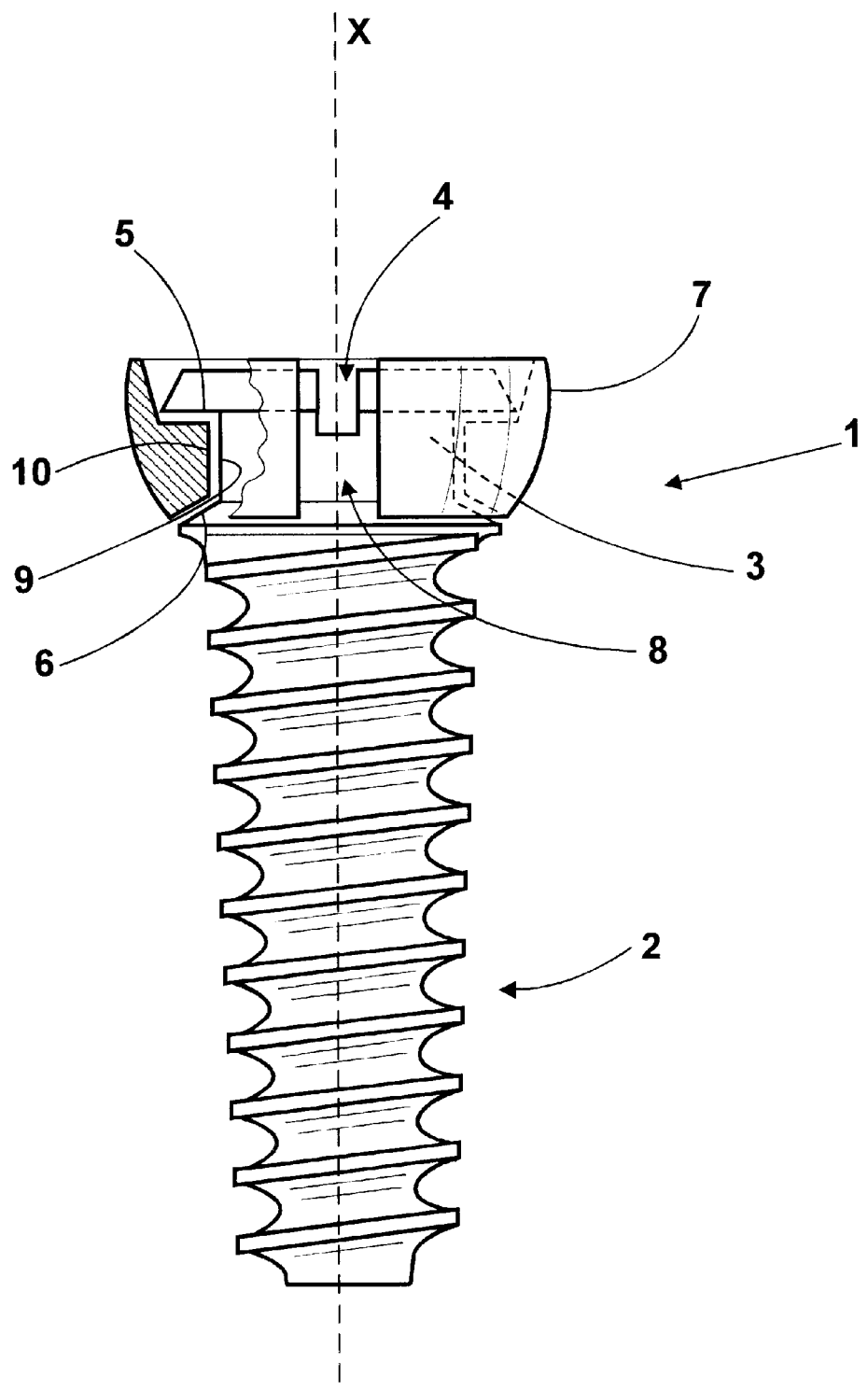
FIG. 1 shows a partially cross-sectional side elevation view of a screw including the resilient retaining means according to the invention.

Now referring in detail to the drawings it may be seen from FIG. 1 a fixation screw 1 forming part of a plate and screw fixation assembly according to the invention. Screw 1 has a lower threaded portion 2 to be screwed into a bone (not shown) and a head 3 provided, as it is well known, with any kind of means, preferably a slot 4, to insert a tool, preferably a screwdriver (not shown), to rotate the screw and screw the same into the bone.

Head 3 is provided with a peripheral annular outer groove 9 defined between an upper flange 5 and a lower flange 6, the groove receiving with free rotary movement an annular projection 10 of a resilient cap 7 forming resilient self-retaining means to retain the screw into a plate to which reference will be made hereinafter. Projection 10 is a shoulder extending inwardly radially extending from cap 7.

The resilient retaining means are formed by cap 7 having a cup shape as viewed from a side elevation view, upwardly open at an upper part, forming an upper open to accede to slot 4 by a screwdriver. Cap 7 is retained in groove 9 with free radial and rotary movement and prevented from any axial movement relative to the screw.

Figure 2A:
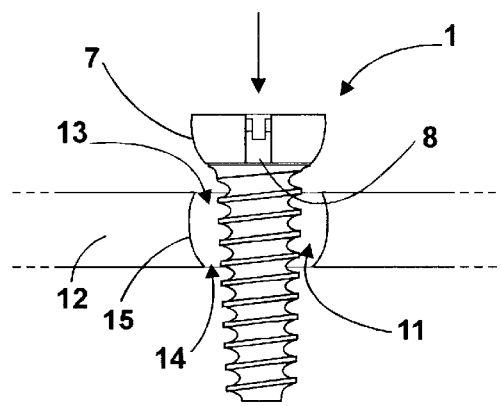
FIG. 2A–2C shows four diagrammatic side elevation views of the plate and screw assembly of the invention with the screw shown in several situations during the insertion thereof in the orifice of the plate.
Figure 2B:
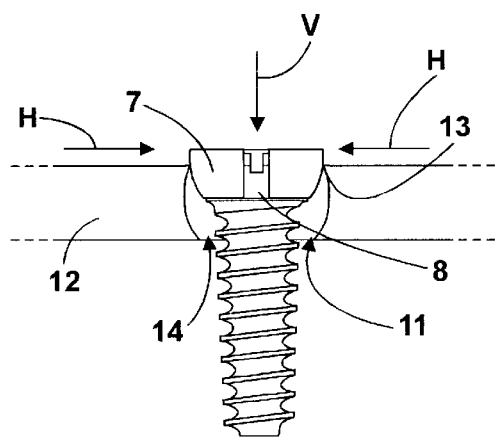
Figure 2C:
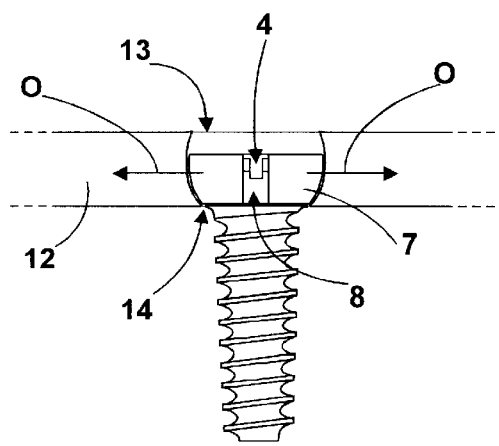

As viewed from a top view indicated by the arrow of FIG. 2A, cap 7 has a "C" shape because of a slot 8 extending axially along a section of the cap, thus defining a split cap having a resilient C-configuration capable of inwardly radially yielding as indicated by the arrows of FIG. 2B and capable of outwardly radially expanding back as indicated by the arrows of FIG. 2C. The general outer configuration of cap 7 is semi-spherical. Cap 7 is to be housed in a cavity 11 formed in an orifice passing through a plate 12 of the plate and screw assembly of the invention.

Cavity 11 preferably defines an at least partially spherical cavity with an upper opening 13 and a lower opening 14, and an intermediate portion being defined inside the cavity between the openings, the intermediate portion having a diameter larger than the diameter of the upper and lower openings, this diameter being the same for both the upper and lower openings or each opening having a diameter distinct to the other.

Although plate 12 is illustrated with only one orifice and cavity 11, it is well known to any person skilled in the art that plate 12 may be provided with a plurality of orifices and it will have several shapes to accommodate the shape of the bone or bones to be fixed together.

According to the principles of the invention, and as it will be explained herein below in connection to the use of the invention, the object of the retaining means formed by cap 7 is to avoid the use of any additional element to guarantee the firm retention of screw 1 against plate 12 for a very long time, after the installation of the plate onto the bone or bone parts to be fixed together, enough to allow the parts to be welded as it is well known for the persons skilled in the art.

While the inventive plate and screw assembly provides the means for safe retention, the screw of the invention behaves like any conventional screw when is being installed and screwed in the bone, through the plate, and a firm retention is guaranteed once the screw is screwed with head 3 and cap 7 being housed and nested inside cavity 11 and the screw being prevented from moving axially back out of the cavity.

During installation and operation of the inventive assembly, the bone or bone pieces (not shown) to be fixed together are placed in the appropriate relative position and plate 12 is placed against the bone or bone pieces. Then, orifices are drilled in the bones each orifice being for receiving a corresponding fixation screw. With appropriate techniques, the fixation screws could be directly screwed in the bones without pre-drilling the necessary orifices.

Figure 2D:
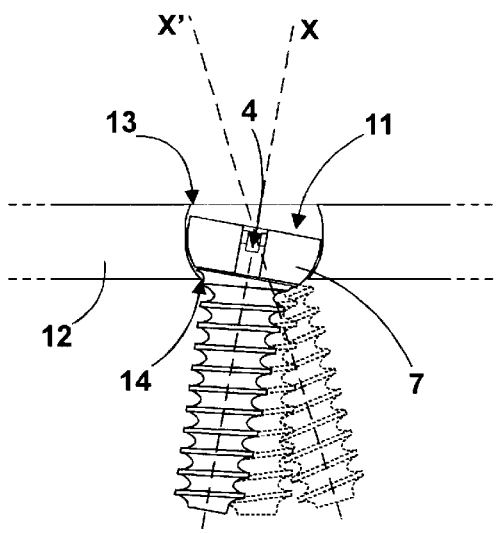
FIG. 2D shows a view similar to FIGS. 2A–2D, with the screw in several pivoting positions, some of them in phantom lines, once the head of the screw is nested in the cavity of the plate.

Although the insertion of only one screw will be described, it is obvious that the installation of the remaining screws will be in the same way. Screw 1 is inserted into, and passed through, the orifice defining cavity 11 so that threaded portion 2 threadably enters the bone and is firmly retained into the same. Because of the spherical configuration of cavity 11 and cap 7, screw 1 may be inserted in an angular configuration with its axis X angularly located relative to a direction normal or perpendicular to plate 12. Thus, screw 1 may adopt several angular positions like X or X' in FIG. 2D. Once cap 7 is entirely nested within cavity 11, cap 7 and head 3 remains firmly accommodated and seated against the cavity wall as shown in FIGS. 2C and 2D.

FIG. 2A shows the screw moving in the direction indicated by the arrow with threaded portion 2 freely passing through cavity 11 and head 3 just before entering cavity 11. With a slight pressure onto the screw head 3 starts to enter cavity 11 as it is shown by FIG. 2B wherein head 3 is partially inside cavity 11 entering in the direction shown by arrow V. In this position, cap 7 starts to radially inwardly yield as indicated by arrows H to pass through the diameter of upper opening 13 of cavity 11. Once inside cavity 11, as shown in FIG. 2C, cap 7 radially outwardly expands back, as indicated by arrows O, to accommodate to the inner wall of cavity 11 and seat inside cavity 11 in any variety of angular positions as shown in FIG. 2D. The insertion of head 3 and cap 7 into cavity 11 in the direction of arrow V is facilitated by the outer spherical configuration of cap 7 requiring only a slightly force to enter cavity 11. However, head 3 and cap 7 could only move axially back out of cavity 11 with a force larger than the force to place cap 7 inside cavity 11 because once the largest diameter of the spherical cap is inside cavity 11 a strong force is required to inwardly radially compress cap 7 to allow head 3 and cap 7 moving out of cavity 11.

Under the above explained conditions, the resilient cap is retained in the head against any axial movement and is capable of radially normally yielding relative to the screw axis to enter into cavity 11 and radially normally expanding back relative to the screw axis to be retained into cavity together with the head of the screw once inside the cavity, whereby the head of the screw, and hence the screw, being prevented from axially moving back out of the cavity.

While preferred embodiments of the present invention have been illustrated and described, it will be obvious to those skilled in the art that various changes and modifications may be made therein without departing from the scope of the invention as defined in the appended claims.

I claim:

1. Plate and screw assembly for use in bone fixation, applied in procedures of joining bone pieces for the welding of the pieces, comprising:

a plate including at least one orifice passing through the plate defining a housing cavity for housing a head of the screw passing through the orifice to retain the plate against the bone pieces to be joined together, wherein the housing cavity has an upper opening and a lower opening, and an intermediate portion between the openings having a diameter larger than any diameter of the upper and lower openings;

a screw having a longitudinal axis and a screw head; and a resilient cap, the screw head having a peripheral annular outer groove defined between an upper flange and a lower flange of the screw head and the cap having an inwardly radially extending shoulder housed within the groove to retain the cap around the screw head with free radial and rotary movement and prevented from axial movement relative to the screw, and the cap being capable of radially compressing relative to the screw axis to enter into the cavity through the upper opening and radially expanding back relative to the screw axis when in the cavity intermediate portion to be retained in the cavity with the screw head once inside the cavity to prevent the head and the screw from axially moving out of the cavity.

2. The assembly of claim 1, wherein said cavity is part spherical and the resilient cap is received with pivotal movement inside the housing cavity intermediate portion.

3. The assembly of claim 1, wherein the resilient cap is cup-shaped, having an outer part-spherical configuration, with an upper opening to provide access to the screw head by a tool.

4. The assembly of claim 1, wherein the cap is a split cap with a slot extending axially along a section of the cap, whereby the cap has a C-configuration.

5. Plate and screw assembly for use in bone fixation, applied in procedures of joining bone pieces for the welding of the pieces, the assembly comprising:

a plate including at least one orifice passing through the plate, the orifice defining a housing cavity for housing a head of the screw passing through the orifice to be screwed into one of the bone pieces to firmly retain the plate against the bone pieces to be joined together, a screw having a head, a resilient retaining means, the screw head having a peripheral annular outer groove defined between an upper flange and a lower flange of the screw head and wherein the resilient retaining means has an inwardly radially extending shoulder housed within said groove to retain the cap around the screw head with free radial and rotary movement and prevented from axial movement relative to the screw, the cap having in a relaxed state an outer diameter greater than the diameter of the orifice entry and less than the diameter of the interior of said housing cavity whereby it is capable of being retained, together with the screw head, inside the housing cavity against any axial movement, and whereby the head of the screw is prevented from axially moving back out of the cavity.

6. The assembly of claim 5, wherein the cap is a split cap with a slot extending axially along a section of the cap, whereby the cap has a C-configuration.

* * * * *